(12) United States Patent
Kreuter et al.

(10) Patent No.: US 10,369,180 B2
(45) Date of Patent: Aug. 6, 2019

(54) COMPOSITION COMPRISING RETINOL, A PRECURSOR OR A REACTION PRODUCT OF IT AND A PLANT EXTRACT FROM AT LEAST ONE CHAMOMILLA PLANT FOR THE TREATMENT OF CANCER

(71) Applicant: ALPINIA LAUDANUM INSTITUTE OF PHYTOPHARMACEUTICAL SCIENCES AG, Walenstadt (CH)

(72) Inventors: Matthias H. Kreuter, Walenstadt (CH); Jianying Yam, Belp (CH)

(73) Assignee: Alpinia Laudanum Institute of Phytopharmaceutical Sciences AG, Walenstadt (CH)

( * ) Notice: Subject to any disclaimer, the term of this patent is extended or adjusted under 35 U.S.C. 154(b) by 0 days.

(21) Appl. No.: 15/849,109

(22) Filed: Dec. 20, 2017

(65) Prior Publication Data
US 2018/0117108 A1 May 3, 2018

Related U.S. Application Data

(63) Continuation of application No. 13/813,873, filed as application No. PCT/EP2011/003923 on Aug. 4, 2011, now abandoned.

(60) Provisional application No. 61/370,901, filed on Aug. 5, 2010.

(30) Foreign Application Priority Data

Aug. 5, 2010 (EP) ..................................... 10008189

(51) Int. Cl.
| A61K 36/00 | (2006.01) |
|---|---|
| A61K 36/28 | (2006.01) |
| A61K 31/07 | (2006.01) |
| A61K 31/19 | (2006.01) |
| A61K 31/215 | (2006.01) |
| A61K 31/203 | (2006.01) |

(52) U.S. Cl.
CPC .............. *A61K 36/28* (2013.01); *A61K 31/07* (2013.01); *A61K 31/19* (2013.01); *A61K 31/203* (2013.01); *A61K 31/215* (2013.01)

(58) Field of Classification Search
CPC ....................................................... A61K 36/00
USPC ......................................................... 424/725
See application file for complete search history.

(56) References Cited

U.S. PATENT DOCUMENTS

| 5,244,885 | A | 9/1993 | Carle et al. |
|---|---|---|---|
| 5,620,980 | A | 4/1997 | Samour |
| 7,060,306 | B2 | 6/2006 | Springstead |
| 7,148,210 | B2 | 12/2006 | Abraham |
| 8,591,966 | B2 | 11/2013 | Kreuter |
| 2003/0003166 | A1 | 1/2003 | Fleischner |
| 2004/0052880 | A1 | 3/2004 | Kobayashi et al. |
| 2006/0127412 | A1 | 6/2006 | Kakuo et al. |
| 2007/0202593 | A1 | 8/2007 | Liu et al. |
| 2008/0166313 | A1 | 7/2008 | Jochim et al. |

FOREIGN PATENT DOCUMENTS

| CN | 101095706 | 1/2008 |
|---|---|---|
| DE | 4136811 A1 | 5/1993 |
| EP | 0 751 125 A1 | 1/1997 |
| EP | 2004/009538 A1 | 1/2004 |
| EP | 1 506 781 A1 | 2/2005 |
| JP | 10203921 | 8/1998 |
| WO | 2002/058640 A1 | 1/2002 |
| WO | 2002/15860 A1 | 2/2002 |
| WO | 2004/098616 A1 | 11/2004 |
| WO | 2006109898 A1 | 10/2006 |
| WO | 2009/138860 A1 | 5/2009 |

OTHER PUBLICATIONS

Srivastava, Janmejai K. et al., "Antiproliferative and apoptotic effects of chamomile extract in various human cancer cells" Agricultural and Food Chemistry (2007), vol. 55 (23), pp. 9470-9478 (XP002608615, ISSN 0021-8561).
Niles R M, "Recent advances in the use of vitamin A (retinoids) in the prevention and treatment of cancer." Nutrition (2000), vol. 16 (11-12), pp. 1084-1089 (Pubmed: 11118831—XP002608616 ISSN: 0899-9007).
International Search Report (ISR) for PCT/EP2011/003923 dated Sep. 28, 2011, pages.
Written Opinion of the International Searching Authority for PCT/EP2011/003923 dated Sep. 28, 2011.
Chemocare.com: Fluorouracil: Online, URL<http://chemocare.com/chemotherapy/drug-info/fluorouracil.aspx> accessed Mar. 7, 2016, 5 pages.
Fragrance Encyclopedia, Online, URL < http://www.chemikalienlexikon.de/aroinfo/1568-aro.htm> Feb. 26, 2000,4 pages, English Google Translation provided, from, Online, URL<https://translate.google.com/translate?hl=en&sl=de&u=http://www.chemikalienlexikon.de/aroinfo/1568-aro.htm&prev=search>.
Pekic et al. Essential Oil of Chamomile Lugulate and Tubular Flowers; vol. 11, Issue 1, 1999, pp. 16-18, one page abstract provided).
Zekovic et al. Chromatography in Our Investigations of Camomile (*Matricaria Chamomilla* L.); —Chromatographia vol. 39, No. 9/10, Nov. 1994, pp. 587-590.

(Continued)

*Primary Examiner* — Michael V Meller
(74) *Attorney, Agent, or Firm* — McDonnell Boehnen Hulbert & Berghoff LLP

(57) ABSTRACT

The invention relates to a (i) Vitamin A, a reaction product, a metabolite or a precursor of it and (ii) a plant extract of chamomile or an active component thereof, preferably for use in the treatment of cancer. The inventive composition may be provided as a medicament or a pharmaceutical composition. The at least one *Chamomilla* plant typically contained in the inventive compositions preferably comprises *Matricaria recutita*, more preferably flores tubiformis of *Matricaria recutita*. Esters of Retinol typically contained in the inventive compositions typically comprise e.g. Retinyl acetate and a plant extract from the plant *Matricaria recutita*.

4 Claims, 6 Drawing Sheets

(56) References Cited

OTHER PUBLICATIONS

Figure 1:
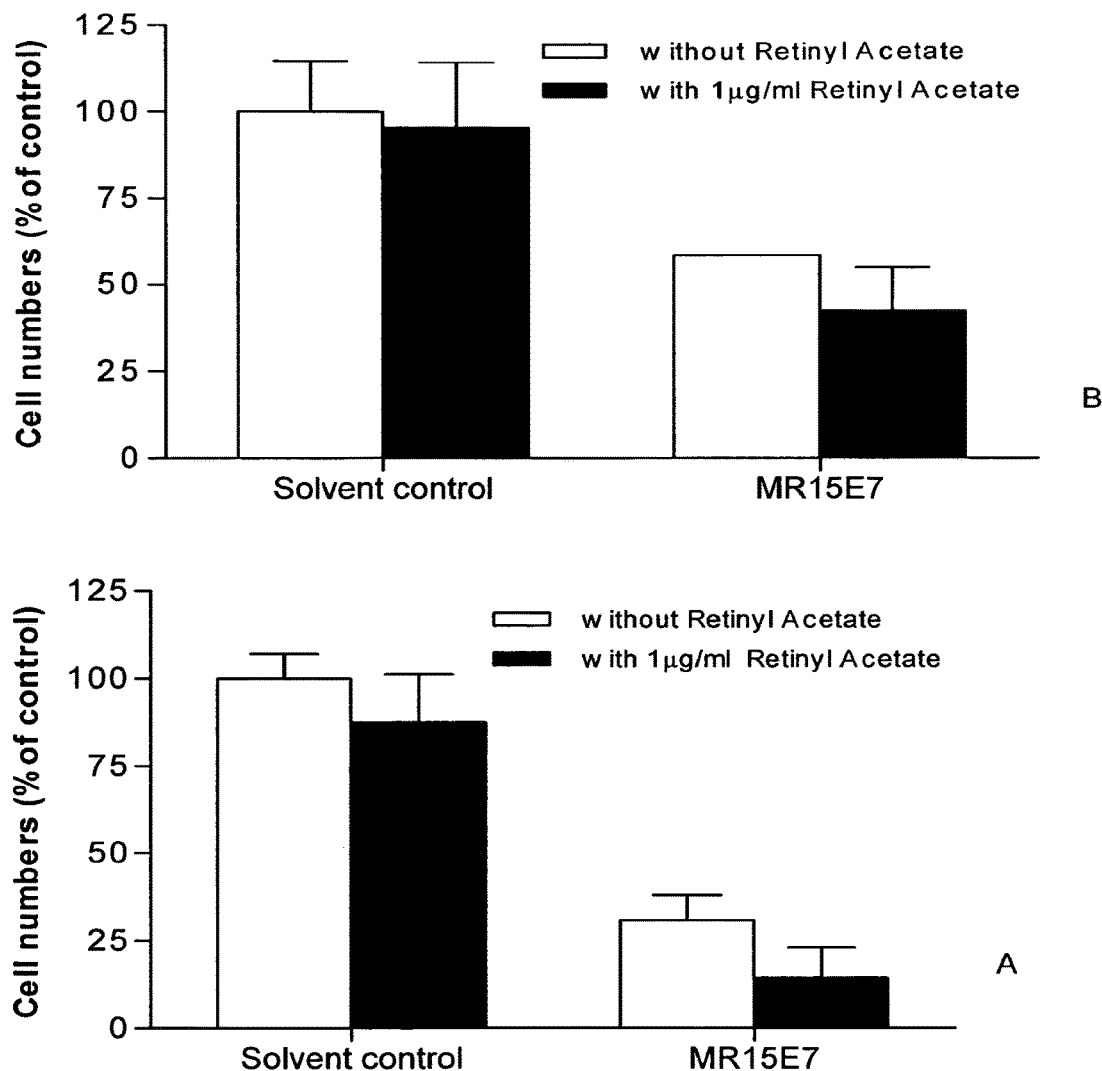

Chamomile: New World Encyclopedia; Online, URL:<http:I/www.newworldencyclopedia.org/entry/Chamomile> 5 pages, accessed Jul. 23, 2014.
Barine et al. The Complex Technology on Products of German Chamomile; Medicina (2003) 39 Tomas, 2 preiedas, pp. 127-131.
Block et al. Safety and Efficacy of Herbal Sedatives in Cancer Care; Integrative Cancer Therapies (Jun. 2004) vol. 3, No. 2, pp. 128-148.
Chamomile (*Matricaria Recutita*), 8 pages, 2016.
Nutrition Facts and Analysis for Tea, herb, chamomile, brewed http:l/nutritiondata.self.com/facts/beverages/4020/2 (Mar. 13, 2016 12:41 :20 PM] Take, 5 pages, 2014.

COMPOSITION COMPRISING RETINOL, A PRECURSOR OR A REACTION PRODUCT OF IT AND A PLANT EXTRACT FROM AT LEAST ONE CHAMOMILLA PLANT FOR THE TREATMENT OF CANCER

This application is a continuation of U.S. Ser. No. 13/813,873, filed on Feb. 1, 2013; which is a U.S. national phase of International Application No. PCT/EP2011/003923, filed Aug. 4, 2011, which claims the benefit of U.S. Provisional Application Ser. No. 61/370,901, filed Aug. 5, 2010, the disclosure of each of which is hereby incorporated by reference in its entirety.

The invention relates to a (i) Vitamin A, a reaction product, a metabolite or a precursor of it and (ii) a plant extract of chamomile or an active component thereof, preferably for use in the treatment of cancer. The inventive composition may be provided as a medicament or a pharmaceutical composition. The at least one *Chamomilla* plant typically contained in the inventive compositions preferably comprises *Matricaria recutita*, more preferably flores tubiformis of *Matricaria recutita*. Esters of Retinol typically contained in the inventive compositions typically comprise e.g. Retinyl acetate and a plant extract from the plant *Matricaria recutita*.

In the recent years many prior art documents have been published, which utilize plant extracts for various purposes, e.g. for therapeutic uses, however, only some of these appear to effectively support or even allow an effective treatment.

In this context, WO 03/101479 A1 discloses a composition having a variety of therapeutic and cosmetic uses comprising various components, particularly (i) an antioxidant or a vitamin; (ii) metal ions, and (iii) an agent that enhances the ability of a cell to take up extracellular components. The antioxidants or vitamins may be e.g. any of vitamins C, A and E, the metal ions are typically selected from e.g. monovalent ions such as Na, K, or from multivalent ions such as FE, Mo, Mg, Mn, Ca, Zn, Cu or Co, typically in the form of a salt. The agent that enhances the ability of a cell to take up extracellular components may be e.g. insulin or a growth hormone or may comprise an antihistamine. The composition of WO 03/101479 A1 is believed to be useful for treating various diseases, e.g., genetic disorders, skin diseases, cancer and viral infections. The composition is typically administered by intramuscular injection. In addition to the composition described in WO 03/101479 A1, further active materials may be given to a subject to be treated. Such active materials may comprise steroids such as estradiol, nandrolone or estriol, or vitamins such as Vitamins A, D and/or E. According to WO 03/101479 A1 the function of vitamin A is to preserve the integrity of epithelial tissue, to play a role in protein synthesis, and to stabilize cell membranes and also subcellular membranes. As shown in the therapeutic Examples in WO 03/101479 A1, these active materials are given separately and do not form part of the composition. E.g. Vitamin A was given separately every week. Furthermore, estriol was given separately every day. Finally, nandrolone decanoate was given separately every 20 days. Even though the composition according to WO 03/101479 A1 appears to provide some advantageous properties in the treatment of diseases such as genetic disorders, skin diseases, cancer and viral infections, the composition according to WO 03/101479 A1 necessarily requires the presence of insulin in the composition, which is not only acting as a utilizer of glucose uptake in the cells but also acts as a growth hormone but in some cases may also enhance the growth of certain types of cancer. For non-diabetic humans, continued insulin intake, e.g. during cancer therapy, may even lead to hypo-glycemia. Furthermore, the antihistamine present in the composition has a sedative side-effect. Besides that, preparation of the medicament is relatively cost intensive due to the high number of components.

Furthermore, WO 2008/146009 A1 discloses a composition comprising an aqueous extract of chamomile flowers for the treatment of a proliferative and/or inflammatory condition. Additionally to the chamomile extract the composition may include black cumin seed oil. According to WO 2008/146009 A1, said extracts can reduce DNA synthesis in human cancer cells and inhibit the production of leucotrienes and IL-6 (interleukin 6). It also has been argued that the inhibition of leucotriene synthesis of the volatile oil is potentiated synergistically in the presence of the seed oil of black cumin (*Nigella sativa*). More precisely, the invention is based on data obtained using an aqueous extract of chamomile flower heads, preferably obtainable by steam distillation, wherein the aqueous extract is composed of the volatile components of the flower heads of *Matricaria recutita* L., also known for those skilled in the art as *Matricariae aetheroleum*, described in PhEur 5.1. The invention is based further on data obtained by using a combination of black cumin seed oil and the volatile oil of the chamomile flower heads. The extracts from WO 2008/146009 A1 already provide a good basis for therapy.

Another composition utilizing plant extracts is described in WO 2009/138860 A1. It discloses a composition comprising an aqueous and/or organic extract of at least one *Chamomilla* plant and/or of at least one *Achillea* plant for the treatment of an abnormal proliferative and/or viral condition, with the proviso that the mono/single extract of *Achillea millefolium* (L.) is excluded from the treatment of said abnormal proliferative condition, and with the further proviso that the mono/single extract of *Matricaria chamomilla* (L.) is excluded from the treatment of said viral condition.

However, none of these prior art documents provides or suggests a composition, which allows to effectively treat cancer, either as a supplementary therapy or as a single therapy. In this context, particularly solid tumours of neurogenic, mesenchymal or epithelial origin and metastases thereof represent a major obstacle.

Accordingly, it is an object of the present invention to provide a composition for the treatment of cancer, preferably solid tumours of neurogenic, mesenchymal or epithelial origin and metastases thereof. It is furthermore an object of the present invention to provide a medicament containing the composition for the treatment of cancer. Preferably, the composition should consist only of compounds essential for the desired activity profile. The composition should also work synergistically, inhibit tumour cell proliferation and induce at least cell death of cancer cells.

The described objectives are solved by the present invention, preferably by the subject matter of the attached claims. More preferably, the present invention is solved according to a first embodiment by a composition comprising or consisting of (i) Vitamin A, a reaction product, a metabolite or a precursor of it and (ii) a plant extract of chamomile or an active component thereof, preferably for use in the prevention, treatment or amelioration of cancer or tumour disease. In some embodiments of the present invention the compositions according to the present invention do not comprise—aside of the plant extract of chamomile—further plant extracts and/or do not comprise plant oil as active ingredient. Most preferably, the inventive composition consists of components (i) and (ii) or contains components (i) and (ii) as the only (pharmaceutically) active ingredients of the inventive composition.

The present invention is based on the surprising finding of the present inventors that a composition comprising (i) Retinol and derivatives thereof and plant extracts of *Matricaria recutita* efficiently inhibits in a synergistic way tumour cell proliferation and induces cell death in a number of tumour cell lines at doses, which have not been shown to be effective to inhibit tumour cell proliferation and induce cell death, when given alone. More surprisingly it was found by the present inventors that Retinol and Retinoic acid, when administered in physiological concentrations, induced together with plant extracts of *Matricaria recutita*, cell death in tumour cells derived from neurogenic and epithelial tumours. The present invention is based on data obtained using an aqueous extract of *Matricaria recutita*, including water steam distillate of *Matricaria recutita*, and on data using an organic extract, especially alcoholic extracts of the tubular flowers of *Matricaria recutita* L., (Flores tubiformis) in combination with an Ester of Retinol (Retinylacetat) or Retinoic acid. The experiments were performed using the human glioblastoma cell lines A172 and U87 and the human large cell lung cancer cell line H460. When incubated with extracts of chamomile, the tumour cells were affected similar to the studies described in WO 2009/138860, while incubated with the inventive composition, a strong increase with respect to the inhibition of tumour cell proliferation and induction of cell death took place, which was not observed in the examples described in WO 2009/138860. Therefore treatment of cancer with chamomile extracts involving retinoids might help generally and in certain sub types of cancer.

The inventive composition may be prepared by admixing the components of the inventive composition, preferably comprising or consisting of (i) Vitamin A, a reaction product, a metabolite or a precursor of it and (ii) a plant extract of chamomile or an active component thereof. In this context, the inventive composition preferably comprises about 50 mg to about 1500 mg, preferably about 50 mg to about 1000 mg, of an chamomile extract as described above, and/or typically about 3 mg to about 90 mg, preferably about 3 mg to about 90 mg Vitamin A, or any of the Vitamin A reaction products, metabolites or precursors as described herein.

According to the first embodiment of the present invention, the inventive composition comprises as a first ingredient (i) Vitamin A, a reaction product, a metabolite or a precursor of it. In this context, Vitamin A is known to be important for normal vision, gene expression, reproduction, embryonic development, growth, and immune function. It is a fat-soluble vitamin that is essential for humans and other vertebrates. Vitamin A comprises of a family of molecules containing a 20 carbon structure with a methyl substituted cyclohexenyl ring (beta-iononic ring) and a tetraene side chain with a hydroxyl group (retinol), aldehyde group (retinal), carboxylic acid group (retinoic acid), or ester group (retinyl ester) at carbon-15. In foods of animal origin, the major form of vitamin A is an ester, primarily retinyl palmitate, which is converted to an alcohol (retinol) in the small intestine. The retinol form functions as storage form of the vitamin, and can be converted to and from its visually active aldehyde form, retinal. The associated acid (retinoic acid), a metabolite that can be irreversibly synthesized from vitamin A, has only partial vitamin A activity, and does not function in the retina or some essential parts of the reproductive system. The term vitamin A also includes precursors of vitamin A, such as provitamin A carotenoids that are dietary precursors of retinal. The term retinoids refers to retinol, its metabolites, and synthetic analogues that have a similar structure. The liver, lung, adipose and other tissues possess carotene 15, 15'-dioxygenase activity and it is presumed that carotenes may be converted to vitamin A as they are delivered to tissues. The major end products of the enzyme's activity are retinol and retinoic acid. Vitamin A deficiency has been associated with a reduction in lymphocytic numbers, natural killer cells and antigen-specific immunoglobulin responses. A decrease in leukocytes and lymphoid organ weights, impaired T cell function, and decreased resistance to immunologic tumours have been observed with inadequate vitamin A intake. A generalized dysfunction of humoral and cell-mediated immunity is common in experimental animals and is likely to exist in humans (see e.g. "Reference Intakes for Vitamin A. Food and Nutrition Board, Institute of Medicine, 2001"). Accordingly, in the context of the present invention, Vitamin A, a reaction product, a precursor or a metabolite there from, typically comprises as Vitamin A or a derivative thereof, preferably e.g. retinoic acid, all-trans-retinoic acid, 13-cis-retinoic acid, esters of Vitamin A, including retinyl palmitate, or retinol, its visually active aldehyde form retinal, retinyl acetate, alitretinoin, as a precursor of Vitamin A preferably beta-carotene, alpha-carotene, gamma-carotene or beta-cryptoxanthine and as metabolite of Vitamin A preferably associated acid (retinoic acid), a metabolite that can be irreversibly synthesized from vitamin A, has only partial vitamin A activity.

It is to be noted that the prior art also discloses an example of the use of a retinoid in cancer treatment in acute promyelocytic leukemia (APL) in supraphysiological concentrations (see Wang, Z. Y., and Chen, Z. (2008) *Blood* 111, 2505-2515). Acute promyelocytic leukemia (APL) is a distinct subtype of acute myeloid leukemia (AML) and is unique from other forms of AML because it responses exceptionally well to all-trans retinoic acid (ATRA). In APL patients, the differentiation program of promyleocytes is halted due to a mutated retinoic acid receptor alpha (RAR-alpha). The mutation is caused by a chromosomal translocation between the promyelocytic leukemia gene (PML) on chromosome 15 and the RAR-alpha gene on chromosome 17 resulting in a fusion protein PML-RAR. This hybrid protein represses gene expression of target genes that are essential for the cell differentiation to granulocytes by binding to a set of co-repressors (CoR) and response elements (RAREs). Much of the therapeutic effect of ATRA appears to be derived from its ability to cause a configuration change of the fusion protein leading to, firstly, dissociation of the CoRs and RAREs and, secondly, increase affinity to coactivator complexes which enables, once again, the transcription of genes necessary for differentiation. In addition, ATRA is also thought to induce ubiquitylation and proteasome-mediated degradation of the PML-RAR fusion protein, resulting in relieving the block to differentiation in APL.

The inventive composition may furthermore comprise according to the first embodiment (ii) a plant extract of chamomile or of an active component thereof.

Such a plant extract of chamomile or an active component thereof is typically derived from at least one *chamomilla* plant, preferably from *Matricaria recutita* or German chamomile. The plant extract of chamomile or an active component thereof is typically derived from the whole plant, more preferably from the flowerheads, even more preferably from tubular flowers of the plant, and likely more preferably from tubular flowers of *Matricaria recutita* L. and most preferably tubular flowers from the inflorescence of *Matricaria recutita* L. In this context, *Matricaria recutita* or German chamomile, also spelled chamomile, is an annual plant of the composite family Asteraceae. Synonyms are: *Chamomilla chamomilla, Chamomilla recutita* (as defined according to the *Flora Europaea* or as described in the European Pharmacopeia (*Matricariae aetheroleum* PhEur 5, corrected. 5.1). *Matricaria chamomilla*, and *Matricaria suaveolens*. Notably, the flower head (capitulum) of the chamomile plant is usually composed of two parts, i.e. the yellow disc-shaped or tubular flowers or florets (flores tubiformis or tubiflorum) and the white radiating flowers or florets (flores ligutatea). It has been found that organic extracts of the tubular flowers of *Matricaria recutita* L. (Flores tubiformis) are suitable for the synchronization and the S-phase arrest of abnormal proliferative mammalian cells, especially of cancer cells. This synchronization takes place due to the induction of ornithine decarboxylase (transfer from $G_0$-phase into $G_1$-phase) and the inhibition of topoisomerase II (accumulation and arrest in the early S-phase). It was also found that the inhibition of topoisomerase II was more than 100-fold stronger with an organic extract than with an aqueous extract (with respect to the concentration for complete inhibition of the enzyme). Due to the fact that the inhibition of the topoisomerase II is crucial for the effectiveness of cell synchronization the inventive composition comprising organic extracts of the tubular flowers of *Matricaria recutita* L. (Flores tubiformis) of the present invention together with Vitamin A, a reaction product or a metabolite thereof or a precursor thereof, are much more potent than the corresponding aqueous extracts.

Even though at least one *chamomilla* plant may be used as a basis for the plant extract of chamomile contained in the inventive composition, plant extracts other than from *Matricaria recutita* or German chamomile are preferably excluded from the scope of the present invention by way of disclaimer.

The plant extract of chamomile or of an active component thereof may be an aqueous and/or organic extract and may be obtained by any suitable procedure or method known to those of ordinary skill in the art. The extract may be obtained by e.g. using an aqueous or organic medium, and separation of the extract from other components, e.g. by filtration, chromatography, supercritical fluid extraction, steam distillation, preferably by methods or procedures known to those of ordinary skill in the art. A preferred procedure for the preparation of an aqueous extract is described in WO 2007/057651 A1, the specific disclosure of which is enclosed herein in its entirety. Preferably, such an extract comprises a multi-component mixture of water-soluble components.

Typically, the plant extract from chamomile may be obtained by adding water to the appropriate plant part to obtain a suspension. The suspension is then usually heated to a temperature below the boiling point of water, e.g. 90-94° C., and then cooled to room temperature. The aqueous extract is then preferably subjected to one or two filtration steps, preferably as described herein.

Preferably, the plant extract of chamomile or of an active component thereof or the inventive composition may be prepared as an ethanolic liquid extract or as a waterfree ethanolic liquid extract. For an ethanolic liquid extract the chamomile or parts thereof, preferably tubular flowers from chamomile, most preferably tubular flowers from the inflorescence of *Matricaria recutita* L, are extracted with ethanol, preferably ethanol absolute, preferably under stirring.

The obtained mixture is then preferably stirred, e.g. for about ½ to 2 hours, preferably for about one hour, e.g. at a temperature of about 30° C. to 50° C., e.g. about 40° C. The preparation is then preferably filtrated to obtain a liquid extract typically with a solid content of less than 2%. A water-free ethanolic liquid extract may be then prepared by methods known to a person of skill in the art for reducing the water content in an organic ethanol containing solution, e.g. by adding to the ethanolic liquid extract Span® 20 (Sigma®) (sorbitan (mono)laurate) and Transcutol® HP (Gattefossé®) (diethylene glycol monoethyl ether), e.g. corresponding to a ratio of 1/2/0.2, and evaporating the ethanol under reduced pressure (e.g. 100 to 25 mbar) and a bath temperature of 30° C. to 50° C., e.g. 40° C. Additionally, the extract may be filtered, if necessary, e.g. a cellulose filter (e.g. TS 4 Filtrox®). Lutrol L44 (BASF) can also be utilized.

Alternatively, the plant extract of chamomile or of an active component thereof or the inventive composition may be prepared as an aqueous extract. For an aqueous extract the chamomile or parts thereof, preferably tubular flowers from chamomile, most preferably tubular flowers from the inflorescence of *Matricaria recutita* L., are extracted with water, preferably aqua dest. or aqua purificata, preferably under stirring. The mixture is typically heated up to a temperature of about 70° C. to 100° C., more preferably to a temperature of about 90° C. to 95° C., preferably in a specific time frame, e.g. 15 minutes to about 2 hours, e.g. about 30 minutes to about 35 minutes. Subsequent the mixture may be cooled down to about 20 to about 40° C., e.g. about 30° C. to about 35° C., may be filtered once or twice or more, e.g. using a deep layer cellulose filter. If necessary, the extract may be treated with 1% m/m of Mygliol 812 N, preferably stirring the extract after addition. Furthermore, the pH of the mixture may be adapted to e.g. about 6 to 7, e.g. to about 6.3 to about 6.7, e.g. with a base, e.g. sodium hydroxide, and optionally micro-filtered, e.g. through a 0.1 µm membrane filter and optionally subsequently through a 1000 kDa ultra filter.

The inventive composition but also the plant extract of chamomile to be used should be suitable for administration, e.g. for oral use, for injection, etc. For this purpose, it is desirable to remove endotoxins, polyphenols, cumarines and (by any suitable means, known to those in the art) large molecular weight component, e.g. those having a molecular weight of more than 1,000 or 10,000 Da.

As described above the aqueous extract after preparation may be subjected to one or two filtration steps, preferably as described herein. Such a filtration step may be selected from filtration techniques such as, for the purposes of illustration only, microfiltration and/or ultrafiltration, respectively. Other techniques, such as use of a lipophilic barrier, also may be suitable. Each filtration step may be conducted in one, two or more than two stages, if desired, combining the same of different filtration techniques. In this context, microfiltration is typically applied in order to remove material that would otherwise compromise the effectiveness of the ultrafiltration step.

Furthermore, the inventive composition and/or the plant extract of chamomile prior to preparing the inventive composition may be purified. A preferred procedure is to purify the initially obtained plant extract, e.g. a volatile oil, an aqueous or organic extract, preferably prior to preparing the inventive composition and/or the inventive composition subsequent to preparation, by contacting it with crosspovidone (crosslinked povidone) and sodiumsulfate. Crosspovidone is known for those skilled in the art to complex phenolic compounds and cumarines. Sodiumsulfate is known to bind residues of water. Separation of the purifying agents results in a plant extract or composition free or nearly free from cumarine, phenol and residual water. After purification the analysis of bacterial endotoxins of the samples obtained may be performed with the Cambrex PyroGene assay, preferably using a dilution factor of 1:10.000.

According to a further embodiment, the present invention provides a pharmaceutical composition comprising the inventive composition as defined herein, preferably comprising or consisting of (i) Vitamin A, a reaction product, a metabolite or a precursor of it and (ii) a plant extract of chamomile or an active component thereof, preferably for use in the treatment of cancer, and optionally a pharmaceutically acceptable carrier and/or vehicle.

The inventive pharmaceutical composition typically comprises a "safe and effective amount" of the active ingredient(s) of the inventive pharmaceutical composition, particularly of the (i) Vitamin A, a reaction product, a metabolite or a precursor thereof, and (ii) a plant extract of chamomile or an active component thereof. As used herein, a "safe and effective amount" means an amount of the active ingredient(s) as defined herein as such that is sufficient to significantly induce a positive modification of a disease or disorder as defined herein. At the same time, however, a "safe and effective amount" is small enough to avoid serious side-effects and to permit a sensible relationship between advantage and risk. The determination of these limits typically lies within the scope of sensible medical judgment. A "safe and effective amount" of the active ingredient(s) of the inventive pharmaceutical composition, particularly of the inventive nucleic acid as defined herein, will furthermore vary in connection with the particular condition to be treated and also with the age and physical condition of the patient to be treated, the body weight, general health, sex, diet, time of administration, rate of excretion, drug combination, the activity of the inventive nucleic acid as defined herein, the severity of the condition, the duration of the treatment, the nature of the accompanying therapy, of the particular pharmaceutically acceptable carrier used, and similar factors, within the knowledge and experience of the accompanying doctor. The inventive pharmaceutical composition may be used for human and also for veterinary medical purposes, preferably for human medical purposes.

The effective dose of the inventive pharmaceutical composition, preferably incorporated in a suitable dosage form as described herein, is thus typically dependent of the type of cancer and the Vitamin A Status of the patient. However a typical content of an effective dose of the inventive pharmaceutical composition, e.g. in form of a capsule, typically comprises about 50 mg to about 1500 mg, preferably about 50 mg to about 1000 mg, of chamomile extract, and/or typically about 3 mg to about 90 mg, preferably about 3 mg to about 90 mg Vitamin A, for example Retinoic acid or any of the Vitamin A precursors, derivatives or metabolites as described herein. The effective dose, in a form as described herein, could be given once a week, once every two or three or four or five or six days, one, two, three or four times daily, etc.

Pharmaceutical compositions as defined herein typically can be formulated by methods known to those skilled in the art preferably utilizing pharmaceutically acceptable components. The term "pharmaceutically acceptable" refers to those properties and/or substances which are acceptable to the patient from a pharmacological/toxicological point of view and to the manufacturing pharmaceutical chemist from a physical/chemical point of view regarding factors such as formulation, stability, patient acceptance and bioavailability.

In this context, a pharmaceutically acceptable carrier and/or vehicle typically includes the liquid or non-liquid basis of the inventive pharmaceutical composition. If the inventive pharmaceutical composition is to be provided in liquid form, the carrier will be typically pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may be used as well for the inventive pharmaceutical composition, which are suitable for administration to a patient to be treated. The term "compatible" as used here means that these constituents of the inventive pharmaceutical composition are capable of being mixed with the inventive nucleic acid as defined herein in such a manner that no interaction occurs which would substantially reduce the pharmaceutical effectiveness of the inventive pharmaceutical composition under typical use conditions. Pharmaceutically acceptable carriers, excipients and solvents must, of course, have sufficiently high purity and sufficiently low toxicity to make them suitable for administration to a person to be treated. Some examples of compounds which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

Administration of the inventive pharmaceutical composition preferably occurs via the respiratory tract, via oral administration or may be administered by injection, typically via parenteral injection, preferably by subcutaneous, intravenous, intramuscular, intra-articular, intra-synovial, intrasternal, intrathecal, intrahepatic, intralesional, intracranial, transdermal, e.g. via transdermal therapeutic delivery systems such as dermal patches, intradermal, intrapulmonal, intraperitoneal, intracardial, intraarterial, and sublingual injection or via infusion techniques. More preferably, administration of the inventive pharmaceutical composition occurs by intravenous or, more preferably, intramuscular injection, yet most preferably by an inhalator as an aerosol or micro/nano-emulsion via the respiratory tract or via oral administration. The composition might also be administered via the gastrointestinal system, e.g. rectally, e.g. via suppositories.

The pharmaceutical composition might be formulated into sterile injectable forms, into oral dosage forms, into tablets, like film tablets, or capsules like soft gelatin capsules or hard capsules, for example hydroxypropylmethylcellulose capsules, troches, lozenges, aqueous or oily suspensions or solutions, dispersible powders or granules, emulsions, syrups or elixirs, suppositories, etc., any of these preferably together with suitable pharmaceutically acceptable carriers and/or auxiliaries/excipients. If desired the pharmaceutical composition might be incorporated in sustained release formulations, e.g. retard tablets, or any kind of dosage forms suitable to reveal optimal bioavailability, solubility and stability of the pharmaceutical composition.

In the above context, sterile injectable forms/preparations of the inventive pharmaceutical compositions may be e.g. (aqueous or oleaginous) suspensions. These suspensions may be formulated according to techniques known in the art using suitable dispersing or wetting agents and suspending agents. The sterile injectable form/preparation may also be a sterile injectable solution or suspension in a non-toxic parenterally-acceptable diluent or solvent, for example as a solution in 1,3-butanediol. Among the pharmaceutically acceptable carriers that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation of the inventive pharmaceutical composition.

The inventive pharmaceutical composition containing the active ingredient(s) may also be preferably in a oral dosage form suitable for oral administration, for example, as capsules, tablets, troches, lozenges, aqueous, or oily suspensions or solutions, dispersible powders or granules, emulsions, hard or soft capsules, or syrups or elixirs. Such compositions may contain one or more agents selected from the group consisting of sweetening agents, flavouring agents, colouring agents and preserving agents in order to provide pharmaceutically elegant and palatable preparations. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the inventive nucleic acid as defined herein, is combined with emulsifying and suspending agents. If desired, certain sweetening, flavouring or colouring agents may also be added. Tablets typically contain the active ingredient(s) in admixture with non-toxic pharmaceutically acceptable excipients such as, for example, inert diluents such as calcium carbonate, sodium carbonate, lactose, calcium phosphate or sodium phosphate; granulating and disintegrating agents, for example corn starch or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated, to form osmotic therapeutic tablets for controlled release. Formulations for oral use may also be presented as hard gelatin capsules wherein the active ingredient(s) is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions in the above context, preferably for oral administrations, for administrations via the respiratory or the gastrointestinal tract or for injectable forms comprising the inventive pharmaceutical compositions, may contain the active ingredient(s) in admixture with suitable excipients. Such excipients are suspending agents, for example sodium carboxymethylcellulose, methylcellulose, hydroxypropylmethyl-cellulose, sodium alginate, polyvinyl pyrrolidone, gum tragacanth and gum acacia; dispersing or wetting agents, for example a naturally occurring phosphatide such as lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, such as a polyoxyethylene with partial esters derived from fatty acids and hexitol anhydrides, for example polyoxyethylene sorbitan monooleate. Aqueous suspensions may also contain one or more preservatives, for example ethyl or n-propyl p-hydroxybenzoate, one or more colouring agents, one or more flavouring agents, and one or more sweetening agents, such as sucrose or saccharin.

Oily suspensions in the above context, preferably for administrations via the respiratory or the gastrointestinal tract comprising the inventive pharmaceutical compositions, may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents (such as those set forth above) and flavouring agents may be added to provide a palatable oral preparation. These compositions may be preserved by the addition of an antioxidant such as ascorbic acid.

Furthermore, dispersible powders and granules suitable for preparation of an aqueous suspension by the addition of water, preferably for administrations via the respiratory or the gastrointestinal tract comprising the inventive pharmaceutical compositions, provide the active ingredient(s) in admixture with a dispersing or wetting agent, suspending agent and one or more preservatives. Suitable dispersing or wetting agents and suspending agents are exemplified above. Sweetening, flavouring and colouring agents may also be present. A pharmaceutical composition for use in the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents. Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated using suitable dispersing or wetting agents and suspending agents, examples of which have been mentioned above. A sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. The composition may also be administered in the form of suppositories for rectal administration of the drug. Such compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Additionally, the inventive pharmaceutical composition may be administered topically, where applicable. Topical administration is particularly preferred, when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be provided typically in the form of, for example, creams, ointments, jellies, solutions or suspensions, preferably containing the active ingredient(s) as defined herein suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

The inventive pharmaceutical composition may additionally comprise a penetration enhancer. Such a penetration enhancer may be selected from any compound suitable for the inventive purpose, e.g. selected from penetration enhancers (also called sorption promoters or accelerants) known to a person of skill in the art, preferably a compound which penetrates into skin to reversibly decrease the barrier resistance. Numerous compounds have been evaluated for penetration enhancing activity, including sulphoxides (such as dimethylsulphoxide, DMSO), Azones (e.g. laurocapram), pyrrolidones (for example 2-pyrrolidone, 2P), alcohols and alkanols (ethanol, or decanol), glycols (for example propylene glycol, PG, a common excipient in topically applied dosage forms, diethylene glycol monoethyl ether (Transcutol®)), surfactants (also common in dosage forms) and terpenes, etc. Many potential sites and modes of action have been identified for skin penetration enhancers; the intercellular lipid matrix in which the accelerants may disrupt the packing motif, the intracellular keratin domains or through increasing drug partitioning into the tissue by acting as a solvent for the permeant within the membrane. Further potential mechanisms of action, for example with the enhancers acting on desmosomal connections between corneocytes or altering metabolic activity within the skin, or exerting an influence on the thermodynamic activity/solubility of the drug in its vehicle are also feasible, and form part of the present disclosure. Even though insulin may be included as a penetration enhancer, it is preferably excluded from the scope of the present invention by way of disclaimer.

The inventive composition or pharmaceutical composition may be used to prevent, treat or ameliorate a disease as defined herein, preferably cancer or a tumour disease, either as a supplementary therapy or as a single therapy. For this purpose, the inventive composition or pharmaceutical composition may be administered via any of the above routes using any of the above defined dosage forms. Furthermore, the inventive composition or pharmaceutical composition may be administered prior, concurrent and/or subsequent to a (conventional) cancer therapy, e.g. a chemotherapy, a surgery, an immunotherapy, etc.

In this context, cancer or a tumour disease preferably includes e.g. solid tumours of neurogenic, mesenchymal or epithelial origin and metastases thereof, colon carcinomas, melanomas, renal carcinomas, lymphomas, acute myeloid leukaemia (AML), acute lymphoid leukaemia (ALL), chronic myeloid leukaemia (CML), chronic lymphocytic leukaemia (CLL), gastrointestinal tumours, pulmonary carcinomas, gliomas, thyroid tumours, mammary carcinomas, prostate tumours, hepatomas, various virus-induced tumours such as, for example, papilloma virus-induced carcinomas (e.g. cervical carcinoma), adenocarcinomas, herpes virus-induced tumours (e.g. Burkitt's lymphoma, EBV-induced B-cell lymphoma), heptatitis B-induced tumours (hepatocell carcinoma), HTLV-1- and HTLV-2-induced lymphomas, acoustic neuromas/neurinomas, cervical cancer, lung cancer, pharyngeal cancer, anal carcinomas, glioblastomas, lymphomas, rectal carcinomas, astrocytomas, brain tumours, stomach cancer, retinoblastomas, basaliomas, brain metastases, medulloblastomas, vaginal cancer, pancreatic cancer, testicular cancer, melanomas, thyroidal carcinomas, bladder cancer, Hodgkin's syndrome, meningiomas, Schneeberger disease, bronchial carcinomas, hypophysis tumour, Mycosis fungoides, oesophageal cancer, breast cancer, carcinoids, neurinomas, spinaliomas, Burkitt's lymphomas, laryngeal cancer, renal cancer, thymomas, corpus carcinomas, bone cancer, osteosarcomas, non-Hodgkin's lymphomas, urethral cancer, CUP syndrome, head/neck tumours, oligodendrogliomas, vulval cancer, intestinal cancer, colon carcinomas, oesophageal carcinomas, wart involvement, tumours of the small intestine, craniopharyngeomas, ovarian carcinomas, soft tissue tumours/sarcomas, ovarian cancer, liver cancer, pancreatic carcinomas, cervical carcinomas, endometrial carcinomas, liver metastases, penile cancer, tongue cancer, gall bladder cancer, leukaemia, plasmocytomas, uterine cancer, lid tumour, prostate cancer, etc., particularly solid tumours of neurogenic, mesenchymal or epithelial origin and metastases thereof.

According to a further preferred embodiment, the inventive composition as defined above, preferably comprising or consisting of (i) Vitamin A, a reaction product, a metabolite or a precursor of it and (ii) a plant extract of chamomile or an active component thereof, may be provided as a pharmaceutical composition as defined above, e.g. in the form of a kit or kit of parts. Such a kit or kit of parts may comprise the inventive composition or the inventive pharmaceutical composition either in one part of the kit or in one or more parts of the kit, e.g. one part of the kit comprising Vitamin A, a reaction product, a metabolite or a precursor of it, a further part of the kit comprising a plant extract of chamomile or an active component thereof, and at least one further part of the kit comprising The kit or kit of parts may furthermore contain technical instructions with information on the administration and dosage of the inventive composition or its components, the inventive pharmaceutical composition or of any of its components or parts, e.g. if the kit is prepared as a kit of parts.

In the present invention, if not otherwise indicated, different features of alternatives and embodiments may be combined with each other. Furthermore, the term "comprising" shall not be construed as meaning "consisting of", if not specifically mentioned. However, in the context of the present invention, term "comprising" may be substituted with the term "consisting of", where applicable.

FIGURES

The following Figures are intended to illustrate the invention further. They are not intended to limit the subject matter of the invention thereto.

FIG. 1: shows the potential growth inhibitory effects of retinyl acetate (1 µg/ml), MR15E7 (ethanolic liquid extract) (30 µg/ml) and the combination of 30 µg/ml of the extract and retinyl acetate (1 µg/ml) observed on both the A172 (A) and U87 MG (B) cell lines. The solvent control and the final ethanol concentration for every well was 2%.

Results: It appeared that retinyl acetate at 1 µg/ml did not affect cellular growth in A172 and U87 MG glioblastoma cells as indicated in FIGS. 1A and 1B. The data derived from the experiments described in Example 10, however, showed that MR15E7 reduced A172's cell numbers by 30% to 70% as compared to solvent control (100%). The addition of 1 µg/ml of retinyl acetate further reduced the cellular growth to 14%, demonstrating a clear efficacy enhancement of the combination compared to the compounds alone (FIG. 1A). The effect is also seen similar in the U87 MG (FIG. 1B) but not as strong as observed for the A172.

Figure 2:
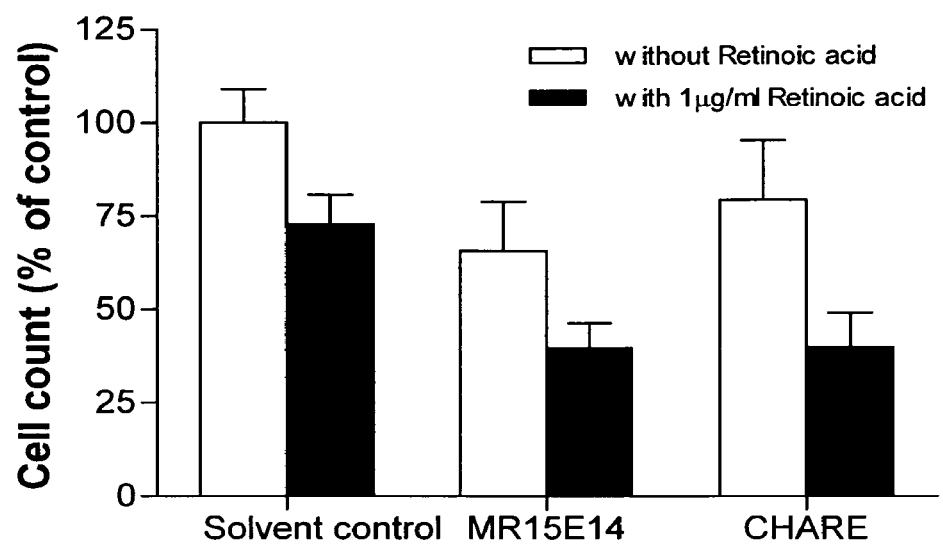

FIG. 2: illustrates the effects of retinoic acid (1 µg/ml), MR15E14 (ethanolic liquid extract) (21 µg/ml), CHARE (aqueous liquid extract) (21 µg/ml) and the combination of the extracts and retinoic acid (1 µg/ml) observed on the H460 cells. The solvent control and the final ethanol concentration for every well was 2%.

Results: As can be seen 1 µg/ml of Retinoic acid, 21 µg/ml of MR15E14 and 21 µg/ml of CHARE slightly reduced the cellular growth of H460 when the cells were treated with the individuals. However, when the same concentration of Retinoic acid was given simultaneously with 21 µg/ml of MR15E14 or CHARE, the anti-proliferative effect was strongly enhanced.

Figure 3:
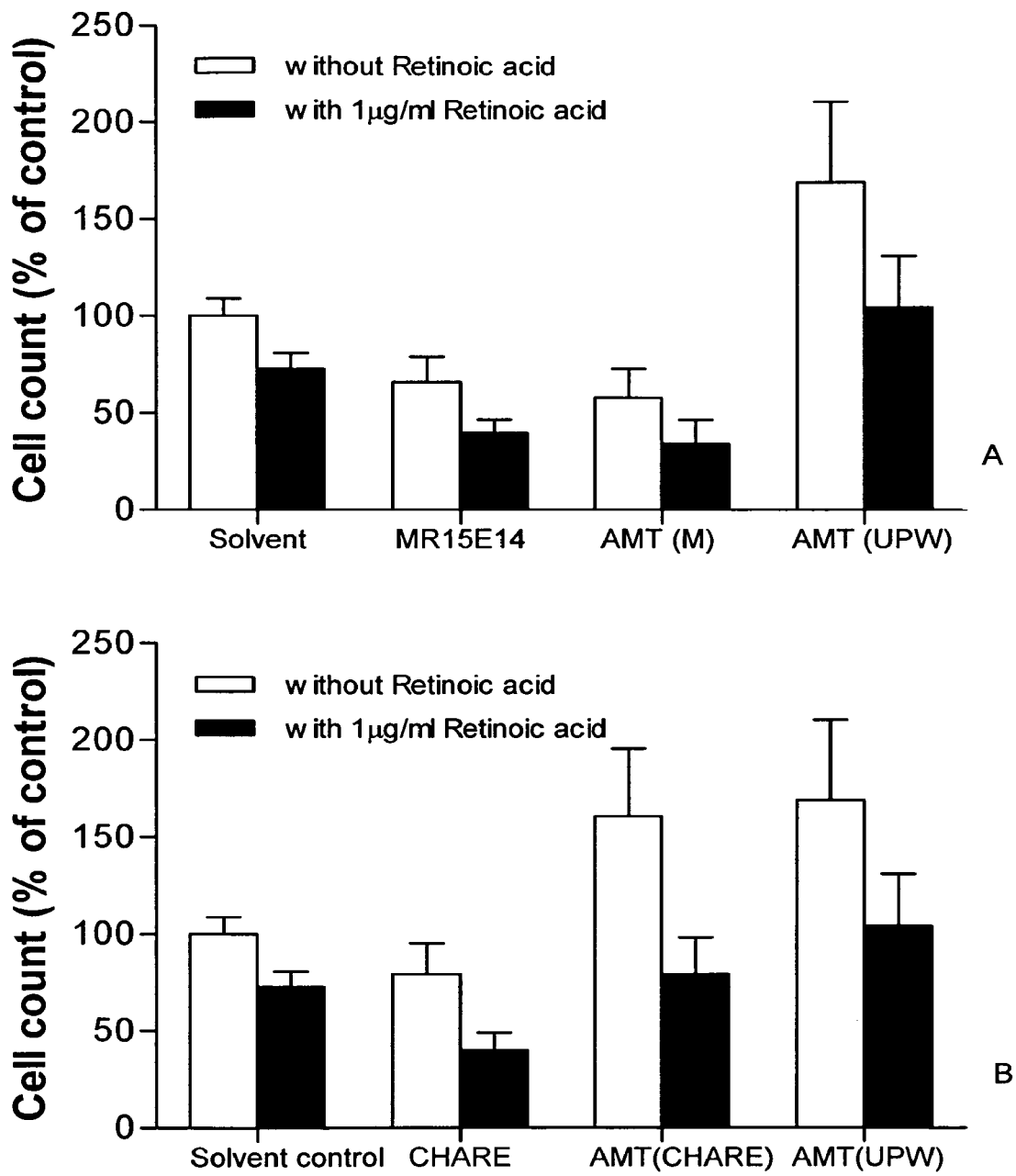

FIG. 3: shows
(A) the treatment of H460 with MR15E14 (ethanolic liquid extract) (21 µg/ml), 1% AMT(M) and 1% AMT (UPW) on H460 in combination with retinoic acid (1 µg/ml) or vehicle control (1% Ethanol).
(B) the treatment of H460 with CHARE (aqueous liquid extract) (21 µg/ml), 1% AMT(CHARE) and 1% AMT (UPW) on H460 in combination with retinoic acid (1 µg/ml) or vehicle control (1% Ethanol). H460 cells were incubation with the sample pairs for a total of 6 days with one dose and media refreshment.

Results: As already earlier seen in FIG. 2, retinoic acid itself showed a slight growth retarding effect on H460 large cell lung cancer cells and again the results indicate a synergistic effect between the chamomile extracts and retinoic acid in reducing cellular growth of H460. The addition of the AMT components to the chamomile extracts did not enhance this effect (FIG. 3A) and, even worse, addition of AMT components promoted cell proliferation in some cases (FIG. 3B). When the components of AMT were tested alone (without Chamomile extracts) they markedly increased cell numbers by more than 50% (FIGS. 3A and 3B). AMT containing the aqueous extract according Example 4 (CHARE) also caused an increase in cell growth. This was not seen with the ethanolic extract according Example 2 (MR15E14), probably as the antiproliferative activity is already alone somewhat stronger than seen for the aqueous extract. Addition of retinoic acid abolished the growth promoting effect of AMT (UPW) and as also seen in the previous pharmacological Examples 10 and 11 enhanced the anti-proliferative effects of both chamomile extracts. The results demonstrate the advantages of the use of a combination solely composed of chamomile and retinoic acid and the disadvantage of the complex mixture of compounds found in AMT.

Figure 4:
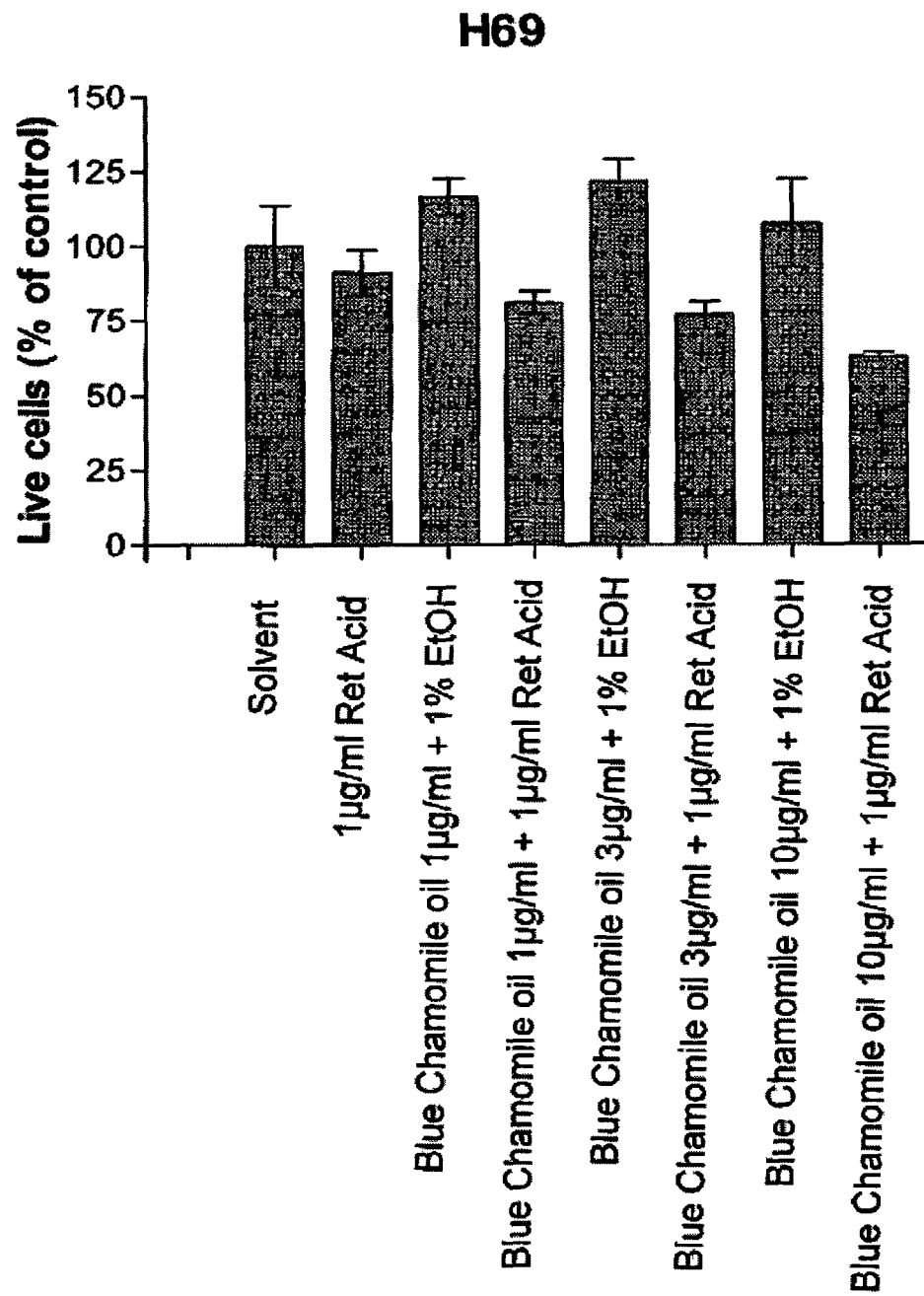

FIG. 4: shows the treatment of H69 cells with Blue Chamomile oil (in different concentrations) in combination with retinoic acid (1 µg/ml) or vehicle control (1% Ethanol), and control experiments The cells were incubated with solvent, 1 µg/ml Retinoic Acid, Blue Chamomile oil 1 µg/ml+1% EtOH, Blue Chamomile oil 1 µg/ml+1 µg/ml Retinoic Acid, Blue Chamomile oil 3 µg/ml+1% EtOH, Blue Chamomile oil 3 µg/ml+1 µg/ml Retinoic Acid, Blue Chamomile oil 10 µg/ml+1% EtOH, Blue Chamomile oil 10 µg/ml+1 µg/ml Retinoic Acid (from left to right). As can be seen, a combination of Blue Chamomile oil 10 µg/ml+1 µg/ml Retinoic Acid showed the best inhibitory effects on H69 cells.

Figure 5:
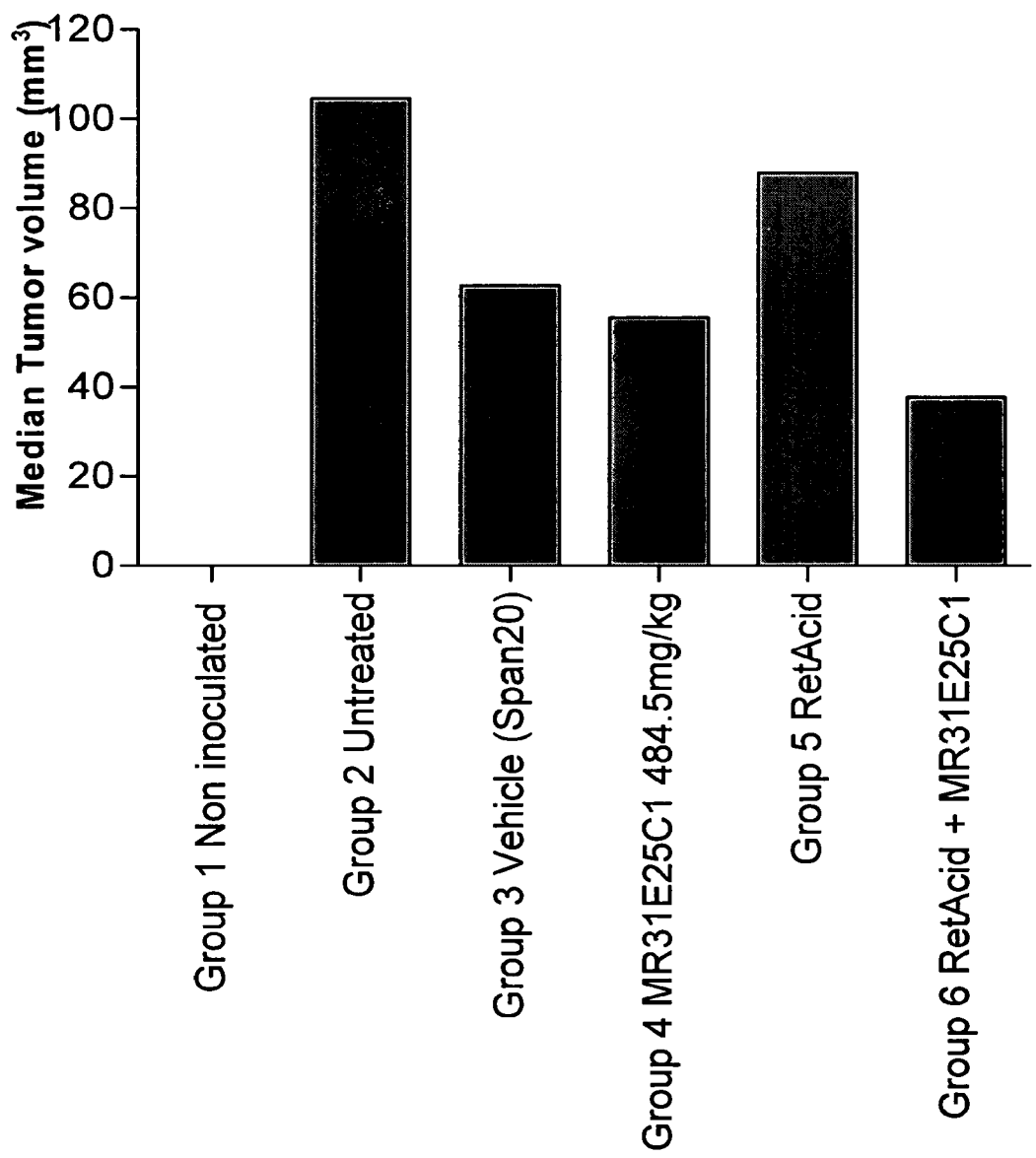

FIG. 5: shows the median tumor volume of female C57BL/6 mice after injection of Pan02 tumor cells and treatment with Vehicle (Span20), MR31E25C1, Retinoic Acid or a combination of MR31E25C1 and Retinoic Acid. After 21 days, the groups treated with MR31E25C1 and in combination with Retinoic acid had reduced tumor volume in comparison to the tumor-bearing untreated animals. The effect was however not observed in the group administrated only with Retinoic acid. As a matter of fact, treatment with Retinoic Acid alone even aggravated the situation in comparison to administration of Vehicle alone.

Figure 6:
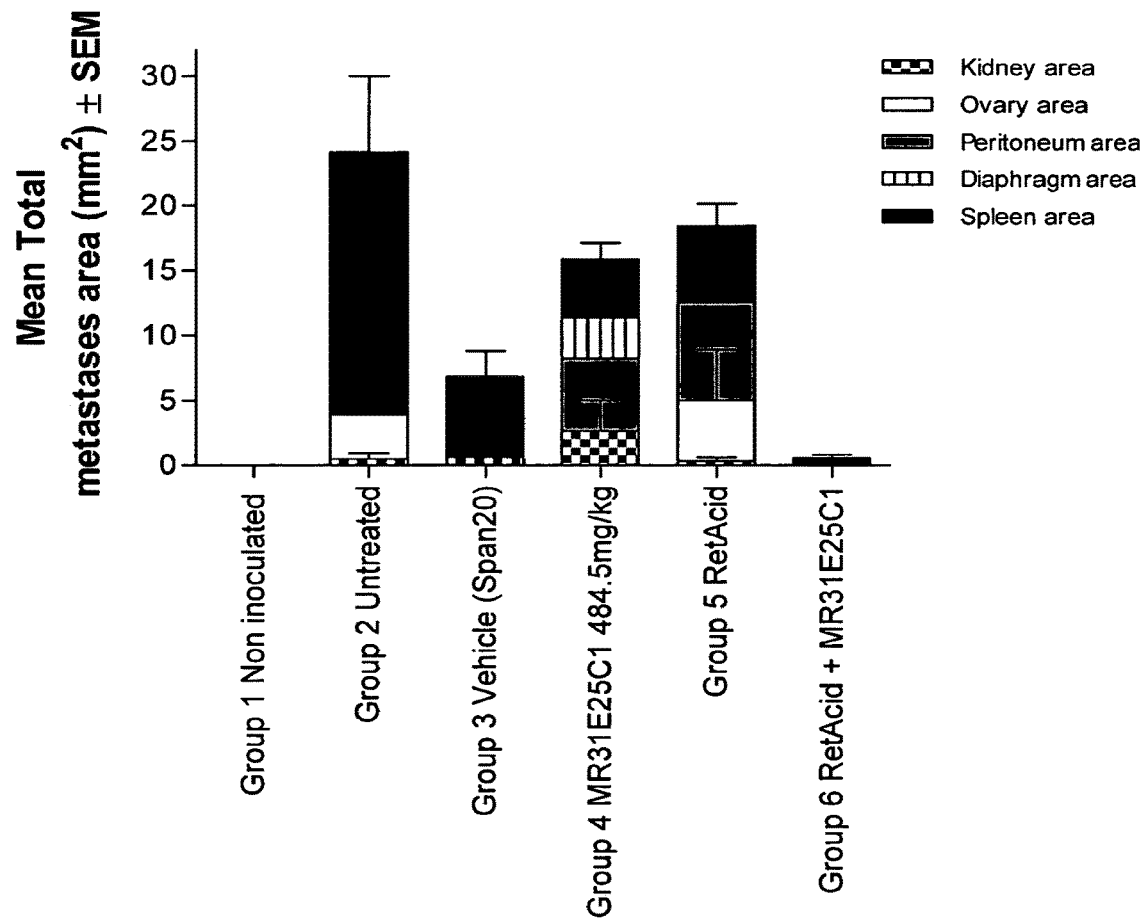

FIG. 6: shows the mean total metastases are for female C57BL/6 mice for the kidney area, ovary area, peritoneum are, diaphragm area and spleen are after injection of Pan02 tumor cells and treatment with Vehicle (Span20), MR31E25C1, Retinoic Acid or a combination of MR31E25C1 and Retinoic Acid. The stacked bar graph reflects the cumulative metastases area measured in various organs per group. Animals treated with MR31E25C1 only or with Retinoic acid only resulted in only slight reduction of the overall metastasis development compared to the untreated PAN02 inoculated group. Strikingly the MR31E25C1 in combination with the Retinoic Acid treatment led a marked regression of metastases in group 6.

TECHNOLOGICAL EXAMPLES OF EXTRACT AND TEST COMPOUND PREPARATIONS

The following Examples are intended to illustrate the invention further. They are not intended to limit the subject matter of the invention thereto.

Example 1 (Preparation of an Ethanolic Liquid Extract MR15E7)

200 g of tubular flowers from the inflorescence of *Matricaria recutita* L. were extracted in a turbo mixer (3×1 min. at 8000 rpm, Eberbach®) with 1500 g ethanol absolute, corresponding to a drug solvent ratio of 1/7.5 (w/w). The obtained mixture was stirred for one hour at a temperature of 40° C. The preparation was then filtrated twice over a deep layer cellulose filter (AF 15 Filtrox®).

1266 g of a clear brownish liquid extract with a solid content of 1.05% (m/m) were obtained.

Example 2 (Preparation of an Ethanolic Liquid Extract MR15E14)

200 g of tubular flowers from the inflorescence of *Matricaria recutita* L. were extracted in a turbo mixer (3×1 min. at 8000 rpm, Eberbach®) with 1500 g ethanol absolute, corresponding to a drug solvent ratio of 1/7.5 (w/w). The obtained mixture was stirred for one hour at a temperature of 40° C. The preparation was then filtrated twice over a deep layer cellulose filter (AF 15 Filtrox®).

1262 g of a clear brownish liquid extract with a solid content of 0.99% (m/m) were obtained.

Example 3 (Preparation of a Water-Free Liquid Extract MR15E7C1)

To 1266 g of an ethanolic liquid extract obtained (contains 13.3 g native extract) in analogy to example 1 were added 26.6 g Span® 20 (Sigma®)(sorbitan (mono)laurate) and 2.66 g Transcutol® HP (Gattefossé®) (diethylene glycol monoethyl ether), corresponding to a ratio of 1/2/0.2. The ethanol was evaporated under reduced pressure (100 to 25 mbar) and a bath temperature of 40° C. 45 g of a brownish liquid extract with precipitate were obtained.

The 15.5 g native extract obtained was adjusted with 4.72 g Span® 20 (Sigma®) and 0.47 g Transcutol® HP (Gattefossé®) in respect of the 1/2/0.2 ratio. Also 100 ml of ethanol absolute were added to this mixture. The ethanol was evaporated under reduced pressure (80 to 25 mbar) and a bath temperature of 40° C. 50 g of a brownish liquid extract with precipitate were obtained.

Afterwards the extract was filtrated at 40° C. over a cellulose filter (TS 4 Filtrox®). 29 g of a brownish free-flowing liquid extract were obtained.

The content of water was found to be 0.64% (w/w).

Example 4 (Preparation of an aqueous liquid extract CHARE) CHARE (AMT2003 Cam) was supplied by Auron Healthcare GmbH (Lot: 86118G001). It had a solid content of 11.68 mg/ml. The extract was prepared as follows: To 300.000 kg Aqua purificata 15.800 kg of tubular flowers from the inflorescence of *Matricaria recutita* L. were given under gentle stirring. The mixture was heated up to 90-95° C. in 30-35 minutes. Subsequent the mixture was cooled down to 30-35° C. and was then filtrated twice over a deep layer cellulose filter. 1% m/m of Mygliol 812 N was added to the filtrate and gently stirred for 10 minutes. Subsequently the pH of the mixture was adapted to 6.3-6.7 with sodium hydroxyde. Then the filtrate was micro-filtrated first through a 0.22 μm membrane filter, the resulting filtrate through a 0.1 μm membrane filter and the resulting filtrate was subsequently filtrated through a 1000 kDa ultra filter. A clear yellowish colored liquid extract was obtained and 0.7% m/m Phenol puriss were added and the liquid mixed until the Phenol was completely dissolved.

Example 5 (Preparation of Liquid Sample AMT(M))

AMT(M) is a mixture consisting of 4 components;
1) AMT2003 Vit(+): consists of 1.027 mg/ml of Dexpanthenol, 6.845 mg/ml Nicotinamide, 0.685 mg/ml Pyridoxin-HCL, 0.937 mg/ml Riboflavin Sodiumphosphate, 1.712 mg/ml Thiamine-HCL, 41.280 mg/ml Sodium ascorbate and additionally 1.79 mg/ml of Chlorpheniramin maleate and was supplied by Auron Healthcare GmbH (Ch.-B.:84105G005)
2) AMT2003Cal: consists of 0.5 g Calciumgluconate $H_2O$ and 0.8756 g of calciumlactobionate $2H_2O$ and was supplied by Auron Healthcare GmbH (Ch.-B.: 0907000134)
3) AMT2003Ins: contains 100 IE/ml of human Insulin was supplied by Auron Healthcare GmbH (Ch.-B.: 0902000117)
4) MR15E14 (see example 2)

A stock solution of 10% AMT was prepared mixing 0.475 ml of AMT2003 Vit(+)+0.320 ml of AMT2003Cal+0.025 ml of AMT2003Ins+1 ml of MR15E14 (2.1 mg/ml)+8.18 ml of ultra pure water (UPW). Except of compound 4) the composition was prepared according to WO 03/101479 A1 for comparative studies.

The final AMT concentration was 1% and 21 μg/ml for MR15E14.

Example 6 (Preparation of Liquid Sample AMT(CHARE))

AMT(CHARE) is a mixture consisting of 4 components;
1) AMT2003 Vit(+): consists of 1.027 mg/ml of Dexpanthenol, 6.845 mg/ml Nicotinamide, 0.685 mg/ml Pyridoxin-HCL, 0.937 mg/ml Riboflavin Sodiumphosphate, 1.712 mg/ml Thiamine-HCL, 41.280 mg/ml Sodium ascorbate and additionally 1.79 mg/ml of Chlorpheniramin maleate and was supplied by Auron Healthcare GmbH (Ch.-B.:84105G005)
2) AMT2003Cal: consists of 0.5 g Calciumgluconate $H_2O$ and 0.8756 g of calciumlactobionate $2H_2O$ and was supplied by Auron Healthcare GmbH (Ch.-B.: 0907000134)
3) AMT2003Ins: contains 100 IE/ml of human Insulin was supplied by Auron Healthcare GmbH (Ch.-B.: 0902000117)
4) CHARE (see example 4)

A stock solution of 10% AMT was prepared mixing 0.950 ml of AMT2003 Vit(+)+0.640 ml of AMT2003Cal+0.050 ml of AMT2003Ins+0.36 ml of CHARE. The AMT composition was prepared according to WO 03/101479 A1 for comparative studies.

The 100% AMT(CHARE) was further diluted to 10% AMT(CHARE) with UPW.

Example 7 (Preparation of Liquid Sample AMT(UPW))

AMT(UPW) is a mixture of consisting of 4 components;
1) AMT2003 Vit(+): has additionally 1.79 mg/ml of Chlorpheniraminmaleate and was supplied by Auron Healthcare GmbH (Ch.-B.:84105G005)
2) AMT2003Cal: consists of 0.5 g Calciumgluconate $H_2O$ and 0.8756 g of calciumlactobionate $2H_2O$ and was supplied by Auron Healthcare GmbH (Ch.-B.: 0907000134)

3) AMT2003Ins: contains 100 IE/ml of human Insulin was supplied by Auron Healthcare GmbH (Ch.-B.: 0902000117)
4) Ultra pure water A stock solution of 10% AMT was prepared mixing 0.950 ml of AMT2003 Vit(+)+0.640 ml of AMT2003Cal+0.050 ml of AMT2003Ins+0.36 ml of UPW. Except of compound 4) the composition was prepared according to WO 03/101479 A1 for comparative studies.

The 100% AMT(UPW) was further diluted to 10% AMT (UPW) with ultra pure water UPW.

Example 8 (Preparation of Sample Retinyl Acetate)

Retinyl Acetate (R7882, Lot: 029K12721) was purchased from Sigma Aldrich (Buchs, Switzerland). A stock solution of 1 mg/ml was prepared in ethanol absolute. The final concentration used in the experiments was 1 µg/ml in 1% ethanol.

Example 9 (Preparation of Liquid Sample Retinoic Acid)

all-trans-Retinoic acid (95152, Lot:1392337) was purchased from Sigma Aldrich (Buchs, Switzerland). A stock solution of 1 mg/ml was prepared in ethanol absolute. The final concentration used in the experiments was 1 µg/ml in 1% ethanol.

Pharmacological Examples in Cell Culture

Example 10 (Effects of Samples and Retinyl Acetate on A172 and U87's Cellular Growth)

The human glioblastoma cell lines A172 and U87 MG were cultivated in culture medium containing 10% FBS and kept in a humidified incubator at 37° C. and 5% $CO_2$. Cultures used in subsequent experiments were passaged less than 25 times. The cells were seeded at 100,000 cells in T25 cm2 culture flasks (cell concentration of 10,000 cells/ml). MR15E7 and Retinyl Acetate prepared according to examples 1 and 8 respectively were added alone as individual or together in combination (A172 FIGS. 1A and U87 FIG. 1B). The solvent control was 2% ethanol.

Media were replaced once after 3 days of incubation with fresh media and samples. After 6 days, all cells were harvested to be analyzed. The cell number was determined using a cell counter (Countess® automated cell counter, Invitrogen).

Live cells were differentiated from dead cells by adding Trypan Blue. Live cells would be Trypan Blue negative since the dye would be excluded from viable cells.

The number of living cells obtained at the end of the experiment was translated into percent of cell count. Solvent control was set at 100%. The raw data (rd) of each well was then transformed to % cell count using the formula: % cell count=(rd X/rd solvent control)×100. See FIGS. 1A and 1B. The potential growth inhibitory effects of retinyl acetate (1 µg/ml), MR15E7 (30 µg/ml) and the combination of 30 µg/ml of the extract and retinyl acetate (1 µg/ml) were observed on both the A172 (A) and U87 MG (B) cell lines. The solvent control and the final ethanol concentration for every well was 2%.

Results:

It appeared that retinyl acetate at 1 µg/ml do not affect cellular growth in A172 and U87 MG glioblastoma cells as indicated in FIGS. 1A and 1B. The data derived from the experiments described in example 10, however, showed that MR15E7 reduced A172's cell numbers to 30% as compared to solvent control (100%). The addition of 1 µg/ml of retinyl acetate further reduced the cellular growth to 14%, demonstrating a clear efficacy enhancement of the combination compared to the compounds alone (FIG. 1A). The effect is also seen similar in the U87 MG (FIG. 1B) but not as strong as observed for the A172.

Example 11 (Effects of Samples and Retinoic Acid on H460's Cellular Growth)

The human large cell lung cancer cell line, H460, was obtained from the American Type Culture Collection. The cells were cultivated in RPMI-1640 medium containing 10% FBS and kept in a humidified incubator at 37° C. and 5% $CO_2$. Cultures used in subsequent experiments were passaged less than 25 times. The H460 cells were seeded at 14375 cells/well (cell concentration of 10,000 cells/ml) in 12 well plates and were left to adhere overnight.

MR15E14, CHARE and Retinoic acid prepared as described in examples 2, 4 and 9 respectively including a solvent control (2% ethanol) were added to the cells. Media were replaced once after 3 days of incubation with fresh media and samples. After 6 days, all cells were harvested to be analyzed. The cell number was determined using flow cytometry. Live cells were differentiated from dead cells by adding Propidium iodide (PI). Live cells would be PI negative since the dye would be excluded from viable cells.

In short, cells were trypsinized, centrifuged and resuspended in 500 µl of media. 2 µl of PI (1 mg/ml) was added to 400 µl of cell suspension. Since the cells number present in 10 µl of the cell suspension was measured, multiple measurements for each well were taken.

The cell numbers obtained at the end of the experiment was translated into percent cell count. Solvent control was set at 100%. The raw data (rd) of each well was then transformed to % cell count using the formula: % cell count=(rd X/rd solvent control)×100.

The results are depicted in FIG. 2. As can be seen, the effects of retinoic acid (1 µg/ml), MR15E7 (21 µg/ml), CHARE (21 µg/ml) and the combination of the extracts and retinoic acid (1 µg/ml) were observed on the H460 cells. The solvent control and the final ethanol concentration for every well was 2%. As also shown in FIG. 2, 1 µg/ml of Retinoic acid, 21 µg/ml of MR15E14 and 21 µg/ml of CHARE slightly reduced the cellular growth of H460 when the cells were treated with the individuals. However, when the same concentration of Retinoic acid was given simultaneously with 21 µg/ml of MR15E14 or CHARE, the anti-proliferative effect was strongly enhanced.

Example 12 (Effects of AMT without Chamomile, with MR15E14 or with CHARE)

The following experiments were performed to compare the composition of the present invention with the teaching of WO 03101479 A1: The human large cell lung cancer cell line, H460, was obtained from the American Type Culture Collection. The cells were cultivated in RPMI-1640 medium containing 10% FBS and kept in a humidified incubator at 37° C. and 5% $CO_2$. Cultures used in subsequent experiments were passaged less than 25 times. The H460 cells were seeded at 14375 cells/well (cell concentration of 10,000 cells/ml) in 12 well plates and were left to adhere overnight. In one set of the experiment the cells were subsequently incubated with MR15E14 (21 µg/ml), prepared according to example 2, 1% AMT(M), prepared according to example 5 and 1% AMT(UPW), prepared according to example 7, in combination with retinoic acid (1 µg/ml) or vehicle control (1% Ethanol) shown in FIG. 3A.

In another set of the experiment the cells were incubated with CHARE (21 µg/ml), prepared according to example 4, 1% AMT(CHARE), prepared according example to 6 and 1% AMT(UPW), prepared according example 7 in combination with retinoic acid (1 µg/ml) or vehicle control (1% Ethanol) shown in FIG. 3B.

The H460 cells were incubated with the samples and sample pairs for a total of 6 days with one dose and media refreshment. After 6 days, all cells were harvested to be analyzed. The cell number was determined using flow cytometry. Live cells were differentiated from dead cells by adding Propidium iodide (PI). In short, cells were trypsinized, centrifuged and resuspended in 500 µl of media. 2 µl of PI (1 mg/ml) was added to 400 µl of cell suspension. Since the cells number present in 10 µl of the cell suspension was measured, multiple measurements for each well were taken. The cell numbers obtained at the end of the experiment was translated into percent cell count. Solvent control was set at 100%. The raw data (rd) of each well was then transformed to % cell count using the formula: % cell count=(rd X/rd solvent control)×100.

The results are illustrated in FIGS. 3A and 3B. As already earlier seen in FIG. 2, retinoic acid itself showed a growth retarding effect on H460 large cell lung cancer cells and again the results indicate a synergistic effect between the chamomile extracts and retinoic acid in reducing cellular growth of H460. The addition of the AMT components to the chamomile extracts did not enhance this effect (FIG. 4A) and, even worse, addition of AMT components promoted cell proliferation in some cases (FIG. 4B). When the components of AMT were tested alone (without Chamomile extracts) they markedly increased cell numbers by more than 50% (FIGS. 3A and 3B). AMT containing the aqueous extract according example 4 (CHARE) also caused an increase in cell growth. This was not seen with the ethanolic extract according example 2 (MR15E14), probably as the antiproliferative activity is already alone somewhat stronger then seen for the aqueous extract. Addition of retinoic acid abolished the growth promoting effect of AMT (UPW) and as also seen in the previous pharmacological examples 10 and 11 enhanced the anti-proliferative effects of both chamomile extracts. The results demonstrate the advantages of the use of a combination solely composed of chamomile and retinoic acid and the disadvantage of the complex mixture of compounds found in AMT.

Example 13 (Effects of Blue Chamomile Oil)

In this experiment the treatment of H69 cells with Blue Chamomile oil (according to Pharmacopeia: *Matricaria aetheroleum*) in combination with retinoic acid (1 µg/ml) or vehicle control (1% Ethanol), optionally in the presence of Blue Chamomile, was carried out. For this experiment, the human small lung cancer cell carcinoma cell line H69 was first sieved with a 40 µm filter to remove clumps before plating 50,000 cells/well/800 µl (cell concentration of 63,500 cells/ml) in a 12 well plate. Samples were added on the same day and the cells were incubated for a total of 7 days (Samples were: Solvent, 1 µg/ml Retinoic Acid, Blue Chamomile oil 1 µg/ml+1% EtOH, Blue Chamomile oil 1 µg/ml+1 µg/ml Retinoic Acid, Blue Chamomile oil 3 µg/ml+ 1% EtOH, Blue Chamomile oil 3 µg/ml+1 µg/ml Retinoic Acid, Blue Chamomile oil 10 µg/ml+1% EtOH, Blue Chamomile oil 10 µg/ml+1 µg/ml Retinoic Acid). After incubation, the cells were resuspended well before 100 µl of the suspension were transferred to a 96 well plate. Duplicates were made. Equal volume of CyQuant direct detection reagent was then added and incubated for 1 hr at 37° C. Only live cells would be stained. Fluorescence was measured at 480/535 nm. The cell numbers obtained at the end of the experiment was translated into percent cell count. Solvent control was set at 100%. The raw data (rd) of each well was then transformed to % cell count using the formula: % cell count=(rd X/rd solvent control)×100. The results can be seen in FIG. 4 showing the treatment of H69 cells with Blue Chamomile oil in combination with retinoic acid (1 µg/ml) or vehicle control (1% Ethanol). As can be seen, a combination of Blue Chamomile oil 10 µg/ml+1 µg/ml Retinoic Acid showed the best inhibitory effects on H69 cells.

CONCLUSIONS

As shown in the pharmacological examples 10-12 chamomile extracts prepared according to examples 1-4 are effective in inhibiting cancer cell proliferation of different origins. As further shown in examples 10-12, incubation of tumour cells with chamomile extracts together with retinoic acid or retinyl acetate enhanced this anti-tumour activity markedly and resulted at least in tumour cell death. While examples 10-12 resulting only in a moderate and comparatively weak anti-proliferative effect in the case when the Vitamin A derivatives are given alone (the effect seems to be mainly mediated through the differentiating effects of the vitamins) it can be stated that a combination of chamomile extracts with Retinol or derivatives is in fact acting synergistically leading to a pronounced increase in anti tumour activity. It can be presumed further that the combination of the Vitamin A/chamomile pair with further ingredients like those found in AMT is rather contra productive and disadvantageous.

Example 14 (Preparation of a Water-Free Liquid Extract MR15E7C1)

To 350 g of a ethanolic liquid extract obtained (contains 49.21 g native extract) in analogy to example 1 were added 108.26 g Lutrol L44 (BASF, Art. Nr. 50143751, Batch.Nr. WPYF580B), corresponding to a ratio of 1/2.2. The ethanol was evaporated under reduced pressure (100 to 25 mbar) and a bath temperature of 40° C. to obtain a brownish liquid extract. The content of water was found to be 0.4% (w/w). Lutrol L44 thus replaces in this example Span 20 used in example 3 of the present application.

Example 15 (Efficacy Study in the Syngenic Pan02 Tumor Model in Female C57BL/6 Mice)

The purpose of this study was to obtain information about the efficacy of the oral combination of Chamomile extract (MR31E25C1 and Retinoic acid (RetAcid) in a syngenic orthotropic PAN02 tumor murine model.

Young (approximately 7 weeks) female C57BL/6 mice were purchased from the National Cancer Institute (Frederick, Md.) and maintained in Aurigon Life Science GmbH's animal care facility with ad libitum access to water and mouse chow (Ssniff® R/M-H). The animals were divided into groups of 10 animals.

All animals, except those in the non-inoculated control group, were given an intrapancreatic injection of 2.5×105 Pan02 tumor cells each. Pan02 is a murine pancreatic adenocarcinoma cell line syngeneic to the C57BL/6 species. First treatment was given orally 15 days after the inoculation for a total period of 21 days.

Necropsy was performed at the end of the in-life phase or immediately on animals found dead or killed in extremis. The weights of the brain, whole pancreas, pancreatic tumor, spleen, and liver were determined and the number/size of metastases on the surface of the spleen and liver, peritoneal, kidney, ovary, diaphragm metastases, and metastases of the lymph nodes (if applicable) were recorded. Additionally, the size of the pancreatic tumors of the animals was measured.

The groups were as follows:
Group 1: Non-inoculated, untreated control group.
Group 2: Inoculated, untreated control group.
Group 3: Inoculated, vehicle Span® 20; 3× daily.
Group 4: Inoculated, MR31E25C1; 484.5 mg/kg, 3× daily.
Group 5: Inoculated, Retinoic Acid; 25 mg/kg 2× daily for first 2 days, 10 mg/kg 1× daily for the rest of the treatment period.
Group 6: Inoculated, Retinoic Acid; 25 mg/kg 2× daily for first 2 days, 10 mg/kg 1× daily for the rest of the treatment period and MR31E25C1; 484.5 mg/kg, 3× daily.

After 21 days, the groups treated with MR31E25C1 and in combination with Retinoic acid had reduced tumor volume in comparison to the tumor-bearing untreated animals. The effect was however not observed in the group administrated only with Retinoic acid. As a matter of fact, treatment with Retinoic Acid alone even aggravated the situation in comparison to administration of Vehicle alone. With respect to the cumulative metastases area measured in various organs per group, Animals treated with MR31E25C1 only or with Retinoic acid only resulted in only slight reduction of the overall metastasis development compared to the untreated PAN02 inoculated group. Strikingly the MR31E25C1 in combination with the Retinoic Acid treatment led to a marked regression of metastases in group 6.

The invention claimed is:

1. A method of treating a human suffering from lung cancer or brain cancer consisting essentially of administering a therapeutically effective amount of an ethanol chamomile extract from tubular flowers of *Matricaria recutita* and vitamin A to said human suffering from said lung cancer or brain cancer to effectively treat the lung cancer or brain cancer in said human in need thereof.

2. A method according to claim 1, wherein the administering is via the respiratory tract, via oral administration, via injection, or via parenteral injection of the human in need thereof.

3. A method according to claim 1, wherein the method further consists essentially of dimethyl sulphoxide, diethylene glycol monoethyl ether, or a mixture thereof.

4. A method according to claim 1, wherein the amount of the ethanol chamomile extract from tubular flowers of *Matricaria recutita* is about 50 mg to about 1500 mg and the amount of the Vitamin A is about 3 mg to about 90 mg.

* * * * *